United States Patent [19]

Davies

[11] Patent Number: 5,917,022
[45] Date of Patent: Jun. 29, 1999

[54] PROCESS FOR REMOVING ENDOTOXINS

[75] Inventor: Jeffrey Raymond Davies, Ivanhoe, Australia

[73] Assignee: CSL Limited, Parkville, Australia

[21] Appl. No.: 08/532,564

[22] PCT Filed: Feb. 15, 1995

[86] PCT No.: PCT/AU95/00071

§ 371 Date: Oct. 13, 1995

§ 102(e) Date: Oct. 13, 1995

[87] PCT Pub. No.: WO95/22556

PCT Pub. Date: Aug. 24, 1995

[30] Foreign Application Priority Data

Feb. 16, 1994 [AU] Australia ................... PM3884

[51] Int. Cl.$^6$ ............................................. B01D 15/08
[52] U.S. Cl. .................. 530/390.1; 530/415; 210/656; 210/670; 210/692; 522/175
[58] Field of Search ................... 530/390.1, 415; 522/175; 210/656, 670, 692

[56] References Cited

U.S. PATENT DOCUMENTS

| | | | |
|---|---|---|---|
| 3,959,128 | 5/1976 | Harris | 210/24 |
| 4,086,222 | 4/1978 | Lindquist et al. | 260/122 |
| 4,491,660 | 1/1985 | Gendrich et al. | 536/32 |
| 5,188,969 | 2/1993 | Arai et al. | 436/548 |

FOREIGN PATENT DOCUMENTS

| | | |
|---|---|---|
| B-43943/89 | 10/1989 | Australia . |
| B-52992/90 | 4/1990 | Australia . |
| B-56812/90 | 6/1990 | Australia . |
| A-10038/92 | 1/1992 | Australia . |
| 01242105 | 4/1989 | Japan . |
| 07284660 A2 | 10/1995 | Japan . |

OTHER PUBLICATIONS

Johansson, et al. "Elution Behaviour of Some Proteins on Fresh Acid or Base Treated Sephacryl S–200 HR," *Jour. of Chromatography* 457 205–13 (1988).

Serafian, et al. "A Procedure for Pyrogen Decontamination of Sephyacryl S–300," *Biochemical Medicine* 28(2) 237–40 (1982).

Cheil Sugar & Co. Derwent Abstract Accession No. 90–137268 Class No. A61K 45/02. KR 8902–068–B (Cheil Sugar Co.) Jan. 13, 1987.

Morrison, et al. "Bacterial Endotoxins and Host Immune Responses," *Adv. Immunol.* 28: 293–450 (1979).

Pearson. F. "Endotoxin," PYROGENS—*Advances in Parenteral Sciences*/2 3: 23–56 (1985).

Rietschel, et al. "Bacterial Endotoxins," *Sci. American* pp. 54–61 (Aug. 1992).

Weary, M. "Depyrogenation," PYROGENS—*Advances in Parenteral Sciences*/2 12: 203–218 (1985).

YAP, et al."Development Of A Process For The Preparation Of Human Serum Albumin Using Chromatographic Methods," *Biotechnology of Blood Proteins* 227 pp. 143–149 (1993).

Van de Voorde et al. (1983), Biochem. Biophys. Res. Comm. 111, 1015.

Kshirsagar et al., (1984), Clin. Chem. Acta. 143, 265.

Hou et al., (1991), Biochem. Biophys. Acta., 1073, 149.

Yamamoto et al. Two types of entomocidal toxins in the parasporal crystals of *Bacillus thuringiensis* kurstaki. Archives of Biochemistry and Biophysics. vol. 227, No. 1, pp. 233–241, 1983.

Du et al. Removal of endotoxin and purification of protective antigens of *Bordetella pertussis*. Shengwu Huaxue Zazhi. vol. 2, No. 4, pp. 37–42, 1986.

Fedoreeva et al. Isolation and physio–chemical properties of a protein, included in an endotoxin from *Yersinia psuedotuberculosis*. Bioorganicheskaia Khimiia. vol, 15, No. 6, pp. 737–747, 1989.

Minobe et al. Characteristics of immobilized histamine for pyrogen adsorption. Journal of Chromatography. vol. 262, pp. 193–198, Jun. 24, 1983.

Talkad et al. Studies on *Escherichia coili* STb enterotoxin. Mikrooekol. Ther. vol. 15, pp. 237–248, 1985.

*Primary Examiner*—Lila Feisee
*Assistant Examiner*—David S. Romeo
*Attorney, Agent, or Firm*—Foley & Lardner

[57] ABSTRACT

A process for the removal of endotoxin from a biological product such as proteins for therapeutic use, blood plasma fractions, and albumin solutions that contains endotoxins, which comprises contacting said biological product with a cross-linked hydrophilic matrix comprising a copolymer of allyl dextran and N,N'-methylene bisacrylamide under conditions effective to bind endotoxins in said biological product to said matrix, wherein the total amount of endotoxin in said biological product does not exceed the absorptive capacity of said cross-linked hydrophilic matrix, and recovering purified biological product from which endotoxin has been removed as a result of said binding.

10 Claims, 1 Drawing Sheet

PROCESS FOR REMOVING ENDOTOXINS

This application was filed Oct. 13, 1995 under 35 US 371 as a U.S. national stage application of International application PCT/AU95/00071, filed Feb. 15, 1995.

FIELD OF THE INVENTION

This invention relates to a process for the removal of endotoxins from biologically derived products particularly products such as proteins for therapeutic use. The present invention is particularly but not exclusively directed to the removal of endotoxins from blood plasma fractions such as albumin, as well as biological products derived from gram negative bacterial culture, such as *Eschedchia coli* culture.

BACKGROUND OF THE INVENTION

The endotoxins are lipopolysaccharides (LPS) of gram negative bacteria such as *E.coli*, and exist in the outer membrane of the cell envelope. They account for more than half the mass of the outer membrane of the cell envelope and they are constantly shed into the environment of the bacterium (Pearson 1985). The basic unit size of LPS is 10,000 to 20,000. However in aqueous solutions LPS generally exists in vesicles ranging in molecular weight from 300,000 to 1 million (Weary 1985).

The LPS molecule contains 3 distinct chemical regions, the Lipid A region, a central polysaccharide region and the O-antigen region. The Lipid A region resides in the cell membrane when endotoxins are contained within the cell wall. This is linked to a central polysaccharide core and this in turn is linked to the O-antigenic side chain, a repeating oligosaccharide structure which varies with different gram negative species.

The Lipid A region is composed of a glucosamine disaccharide containing phosphate groups and is highly substituted with long chain fatty acids. It is now known that Lipid A is responsible for most, if not all, activity associated with bacterial endotoxins and that endotoxins must be released from the bacterial surface to be effective (Rietschel and Brade 1992). The biological activities induced by endotoxins are extremely diverse. These are mediated through the activation of macrophages and other cellular components which lead to a wide range of biological effects. In mild doses, endotoxins produce moderate fever and stimulation of the immune system which in turn leads to microbial killing. In higher doses, they produce high fever, hypotension disseminated blood clotting and lethal shock.

The presence of endotoxins in biologically derived products (biologicals) prepared for therapeutic use is of major concern due to the diverse and potentially harmful biological activities of these molecules. Maintaining sterility in processes used in the manufacture of biologicals, together with stringent protocols for the preparation of equipment, helps to ensure products are free of endotoxins. However, raw materials used to manufacture biologicals are often not sterile. Indeed, when the source of a biological is from a gram negative bacterial culture (e.g. a method using an *E.coli* fermentation system to express recombinant protein), the endotoxin levels in the starting material will be very high. In practice, maintenance of sterility throughout an entire process is not always possible or cost effective. Therefore it is often desirable to have methods in place which either destroy or remove endotoxins while maintaining the integrity of the therapeutic biological component.

There have been numerous approaches to achieving destruction or removal of endotoxins (Pearson 1985, Weary 1985). These include hydrolysis with acid or base, oxidation, alkylation, heat treatment and treatment with polymicin B. However with each of these approaches the effect of the inactivation method on the desired biological product must be evaluated. Furthermore, while pyrogenic activity may be reduced, often endotoxin components remain and the presence of these endotoxin components may be of no benefit in the final product and could possibly be detrimental. It is therefore preferred to remove these endotoxin components from the final biological product.

Selective binding of endotoxins on charged, hydrophobic or affinity media, or separation on the basis of size can be performed. At pH levels greater than pH2, endotoxin aggregates are negatively charged and will bind to positively charged surfaces such as asbestos or anion exchangers (Weary 1985). Endotoxins will also bind to aliphatic polymers such as polypropylene, polyethylene, polyvinylidene fluoride, polytetrafluoroethylene and hydrophobic chromatographic systems via hydrophobic interactions. Endotoxins can also be specifically removed by affinity chromatography using immobilised polymicin B. Additionally, because endotoxins exist primarily as large molecular weight complexes, they can often be removed from desired components by ultrafiltration or gel filtration methods.

Each of the above mentioned procedures presents a problem. Biological molecules, such as human therapeutic proteins derived from plasma, will in general be positively charged at low pH (i.e. less than pH 4). Although endotoxins are negatively charged at relatively low pH and thus will bind to positively charged resins, many therapeutic proteins are unstable under these conditions. Furthermore, complete resolution between protein and endotoxins cannot always be effected. Hydrophobic chromatographic systems will effectively bind endotoxins but often will also bind the desired biological molecule. Additionally, these hydrophobic chromatographic systems can be difficult to regenerate. Affinity chromatography systems using polymicin B are expensive in terms of media cost. Furthermore, in such systems the support can be difficult to regenerate resulting in a short life for this matrix. Size exclusion chromatography or ultrafiltration can also be used to reduce endotoxin levels. However size exclusion chromatographic systems and ultrafiltration systems will only be useful when there is a substantial size difference between the target biological molecule and the endotoxin molecule. Additionally, size exclusion chromatographic systems suffer from the problem of limited capacity.

The major difficulty in separating endotoxins from proteins lies in designing a support material that exhibits a high specificity for endotoxins but a low specificity for proteins. The ideal support

- should not interact with proteins
- should exhibit a high capacity for endotoxins
- should be able to be regenerated
- should be stable under conditions of operation, including regeneration methods
- should be acceptable for use in the manufacture of therapeutic products.

In work leading to the present invention, it has been found that particular chromatographic gel matrices which have in the past been manufactured and used for gel filtration meet the above criteria, exhibiting a minimal interaction with proteins and a high affinity for endotoxins. Furthermore, it has been established that these matrices are stable under the operational and regeneration systems that have developed for binding of endotoxins and for eluting the bound endotoxin.

SUMMARY OF THE INVENTION

According to the present invention, there is provided a process for the removal of endotoxins from a biological product which comprises contacting said biological product with a cross-linked hydrophilic matrix comprising a copolymer of allyl dextran and N,N'-methylene bisacrylamide under conditions effective to bind endotoxins in said biological product to said matrix, and recovering purified biological product from which endotoxins have been removed.

Preferably, after recovery of the purified biological product, the cross-linked hydrophilic matrix is regenerated under conditions effective to elute bound endotoxins from the matrix.

Throughout this specification, unless the context requires otherwise, the word "comprise", or variations such as "comprises" or "comprising", will be understood to imply the inclusion of a stated integer or group of integers but not the exclusion of any other integer or group of integers.

DETAILED DESCRIPTION OF THE INVENTION

The cross-linked hydrophilic matrix comprising a copolymer of allyl dextran and N,N'-methylene bisacrylamide is preferably a product having the following partial structure:

These products are available commercially as Sephacryl® gel filtration media (Pharmacia, Uppsala, Sweden). The Sephacryl® products are sold as gel filtration media for high resolution standard chromatography from millilitre to thousand litre scale. The gel is a cross-linked hydrophilic matrix which at present is sold as six different products, each with a differing porosity range: Sephacryl® S200HR, S300HR, S400HR, S500HR and S1000SF. Prior to the present invention, there has been no disclosure of the capacity of the Sephacryl® products to bind endotoxins, or of their use in the removal of endotoxins from a biological product.

In a particularly preferred embodiment of the present invention, the cross-linked hydrophilic matrix used for the removal of endotoxins is Sephacryl® S200HR.

The biological products which can be purified by removal of endotoxins in accordance with this invention include products for therapeutic use derived from:

(a) plasma (e.g. albumin, immunoglobulins, clotting factors, protease inhibitors and growth factors);

(b) recombinant or cell culture expression systems (e.g. human growth hormone, interferons, cytokines, insulin monoclonal antibodies);

(c) fermentation systems used in the manufacture of vaccines (e.g. components from bordetella pertussis, cultures used in whooping cough vaccine).

In one particularly preferred embodiment, the process of this invention is used for the removal of endotoxins in the

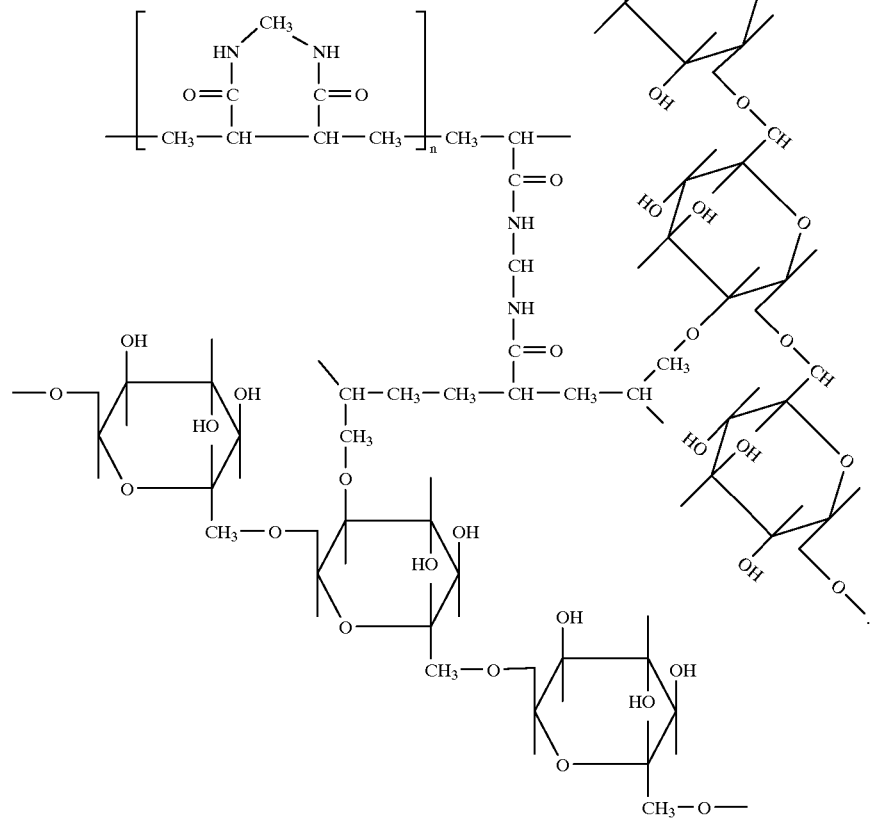

production of albumin by fractionation of blood plasma. Methods for separation and purification of albumin and other protein and lipoprotein components of plasma, particularly human plasma, based on the so-called Cohn fractionation process, have been well known for many years. These methods involve lowering the solubility of protein components of plasma by the addition of ethanol, and fractionation of the plasma under variable conditions of pH, ionic strength, ethanol concentration, protein concentration and temperature. By way of example, one method for the production of albumin using a combination of Cohn fractionation and chromatography is described by Yap et al. (1993).

Whilst the plasma fractionation process is carried out under good manufacturing conditions whereby endotoxin contamination of the albumin or other plasma product is generally avoided, accidental contamination can still occur. This often results in the contaminated product being discarded, or alternatively quite expensive purification steps as previously described need to be employed to remove the endotoxins. The present invention provides a process whereby any endotoxin contamination of an albumin or other plasma fractionation can be readily removed, thereby avoiding uneconomical purification steps or even the need to discard the contaminated product. In addition, the process of the present invention can be carried out in the presence of stabilisers such as tryptophan, and sodium octanoate (or sodium caprylate), which are often used in the stabilisation of albumin solutions during pasteurisation.

Studies on the partitioning of endotoxin on Sephacryl® S200HR demonstrate that it has a high capacity to bind endotoxins (at least 100 EU/mL of gel). Sephacryl® gel matrices have been specifically designed to limit interactions with proteins and for use in the isolation of proteins for therapeutic use, and are designed for use in gel filtration whereby proteins and other biological compounds are separated by size. It has now been established that endotoxins are not resolved on the basis of size using these gel matrices, instead they bind to the matrices and are not eluted under normal aqueous buffer conditions. It has also now been demonstrated that endotoxins can be effectively eluted from Sephacryl® gel matrices using 1M acetic acid, thus allowing the re-use of the matrices. Endotoxins were not eluted from these matrices using 0.1M acetic acid or 0.1M sodium hydroxide, thus indicating that Sephacryl® gel matrices will be effective in binding endotoxins over a broad pH range.

The stability of Sephacryl® gel matrices has been evaluated under acidic and basic conditions, and results of this study showed that the matrices are stable when exposed to 1M acetic acid for short time periods (5 days at 37° C.). Such stability is more than adequate to allow washing with 1M acetic acid to elute bound endotoxins in accordance with the present invention, and a long life and repeated use of Sephacryl® gel matrices can be expected when used under these conditions.

The endotoxin-binding properties of Sephacryl® gel matrices which have now been discovered suggest broad applications for the matrices in the removal of endotoxins from biologically derived products and in particular from blood plasma fractions such as albumin.

Further features of the present invention are more fully described in the following Examples. It is to be understood, however, that this detailed description is included solely for the purposes of exemplifying the present invention, and should not be understood in any way as a restriction on the broad description of the invention as set out above.

EXAMPLES

Example 1

Endotoxin Binding Study.

A. Materials and Methods (i) Endotoxin Concentrate was prepared from a 5% w/v albumin solution which was allowed to become contaminated with microorganisms by exposure to air for several days at room temperature.

(ii) Endotoxin assay. Endotoxin was assayed using a Limulus Amoebocyte Lysate (LAL) test kit (Pyrogent Plus, Bio-Whittaker, Cat. No. N284). Acidic and basic solutions were adjusted to pH 7.0 prior to testing.

(iii) Sephacryl® S200HR (partitioning study): Sephacryl® S200HR (Pharmacia, Uppsala, Sweden) was packed into a column (30 mm diameter×700 mm) and washed in 100 mM sodium acetate pH 5.5 (2 column volumes) then equilibrated in 50 mM sodium acetate pH 6.8 (4 column volumes). Sample was loaded and eluted in the equilibration buffer (flow rate 2 ml/minute).

(iv) Albumin solution: The albumin solution used was a 14% w/v solution in 0.11M sodium acetate, pH 6.8.

B. Results

Figure 1:
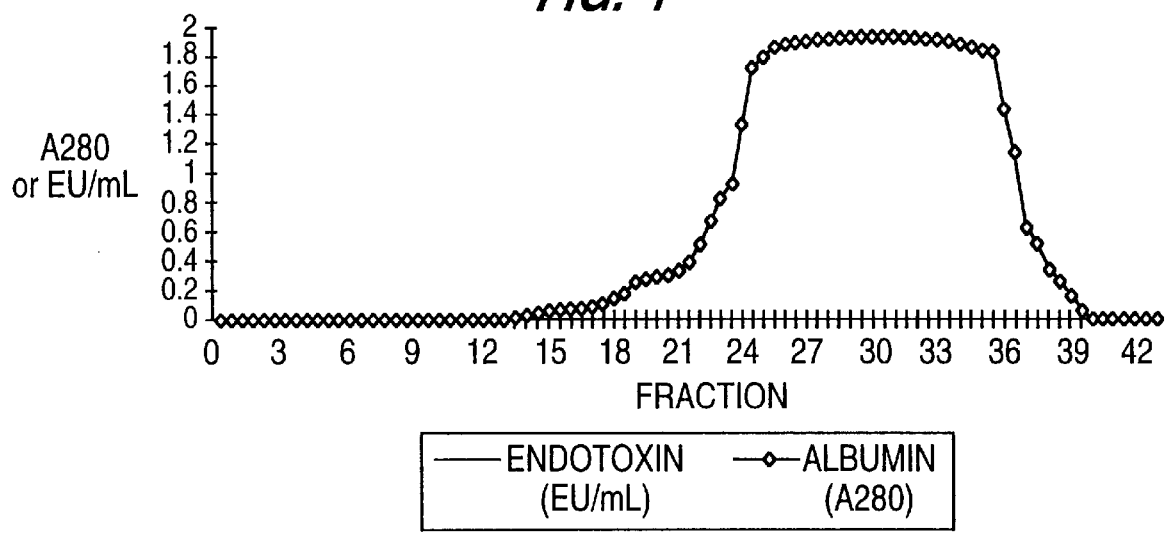
FIG. 1 shows the resolution of endotoxin from albumin monomer by chromatography on Sephacryl® S200HR.

The sample for Sephacryl® S200HR endotoxin partitioning study was prepared by mixing 18 ml of 14% albumin solution with 210 µl endotoxin (450 EU/Ml). A volume of 18 ml was loaded onto the column prepared as described in A(iii). Endotoxin exists generally as high molecular weight complexes (300,000 to 1 million). In this gel filtration system endotoxin was expected to elute in the albumin aggregate, however, no endotoxin was eluted from this system (FIG. 1) indicating that under these chromatographic conditions endotoxin binds to the Sephacryl® S200HR column.

Example 2

The source material used in this Example was albumin, which had been prepared by Cohn fractionation and formulated as a 5% w/v albumin solution in 140 mM NaCl, 8 mM sodium octanoate, pH 7.0. Sephacryl® S200 HR, (Pharmacia) was packed into 3×1 ml columns and equilibrated in buffer (50 mM sodium acetate pH 6.8). On each column 2 ml aliquots of a 5% w/v albumin solution that had an endotoxin content of 37.5 to 54 EU/ml was loaded. The column was then washed with 6 column volumes of equilibration buffer to recover residual albumin followed by 6 column volumes of elution buffer, either (i) 0.1M acetic acid (column 1), (ii) 1M acetic acid (column 2) or (iii) 0.1M sodium hydroxide (column 3). The column washing pool and each of the elution peaks were then assayed for endotoxin using a Limulus Amoebocyte Lysate (LAL) test kit (Pyrogen Plus, Bio-Whittaker). The results, showing the efficacy of the three elution buffers for eluting endotoxin bound to the Sephacryl® S200HR gel matrix, are summarised in Table 1 below.

TABLE 1

Efficacy of eluting agent for endotoxins.

| Fraction | Total Endotoxin | | |
|---|---|---|---|
| | 0.1 M sodium hydroxide | 0.1 M acetic acid | 1 M acetic acid |
| Initial sample | 77 EU | 77 EU | 108 EU |
| 6 column volume wash (albumin peak) | <0.36 EU recovered | <0.36 EU recovered | <0.36 EU recovered |
| 6 column volume with eluting agent | <0.36 EU recovered | <0.36 EU recovered | 95 EU recovered |

The results in Table 1 unequivocally demonstrate that Sephacryl® S200HR is effective in binding endotoxin. The capacity of the matrix to bind endotoxin is shown here to be greater than 100 EU/ml matrix.

The results of these studies with the three eluting agents showed that only 1M acetic acid was effective in eluting endotoxin, with essentially all endotoxin that was applied being recovered. Further work was conducted which demonstrated that two column volumes of 1M acetic acid is sufficient to elute the bulk of bound endotoxin. Washing with 0.1M sodium hydroxide of 0.1M acetic acid was ineffective in eluting bound endotoxin.

Example 3

The source material used in Examples 3 to 5 was albumin manufactured using a combination of Cohn fractionation and chromatography according to the method of Yap et al. (1993). Briefly, the albumin was purified from plasma using Cohn fractionation to separate immunoglobulin from albumin. The crude albumin solution was then purified using ion exchange and gel filtration chromatography. Following ion exchange chromatography, the albumin eluate, in 0.11M sodium acetate, pH 5.5 was adjusted to pH 6.8 and concentrated to approximately 14% w/v albumin. This material was then processed on Sephacryl® S200HR. The albumin monomer was then formulated as 5% w/v albumin, 140 mM NaCl, 8 mM sodium octanoate, pH 7.0.

Sephacryl® S200HR (Pharmacia) was packed into a 1 ml column and equilibrated in buffer (50 mM sodium acetate pH 6.8). Varying amounts of a 5% w/v albumin solution that had a high endotoxin content (30–60 EU/ml) was loaded onto the column in sequential runs. After each run, the column was washed with equilibration buffer (6 column volumes) to recover residual albumin and this was pooled with the unbound albumin. Bound endotoxin was subsequently eluted with 1M acetic acid. The recovered albumin and the 1M acetic acid eluate were then assayed for endotoxin using a Limulus Amoebocyte Lysate (LAL) test kit (Pyrogen Plus, Bio-Whittaker). The results are summarised in Table 2 below.]

TABLE 2

Variable loads of endotoxin onto the column.

| Load volume (ml) | Endotoxin load EU/ml media | Endotoxin in albumin pool (unbound and residual) | 1 M Eluate |
|---|---|---|---|
| 0.6 | 18–36 | <0.06 EU/ml | 23 EU |
| 2.0 | 60–120 | <0.36 EU/ml | 95 EU |
| 3.0 | 90–180 | 2.4 EU/ml | 46 EU |

The results in Table 2 demonstrate that for different loads of endotoxin in albumin, Sephacryl® S200HR is effective in removing endotoxin from the albumin and that this endotoxin is subsequently eluted by 1M acetic acid. After loads of greater than 90 EU/ml, small amounts of endotoxin appear in the albumin pool. The result also demonstrates that the gel can be regenerated as the endotoxin loads were applied sequentially with elution of bound endotoxin after each run.

Example 4

Figure 2:
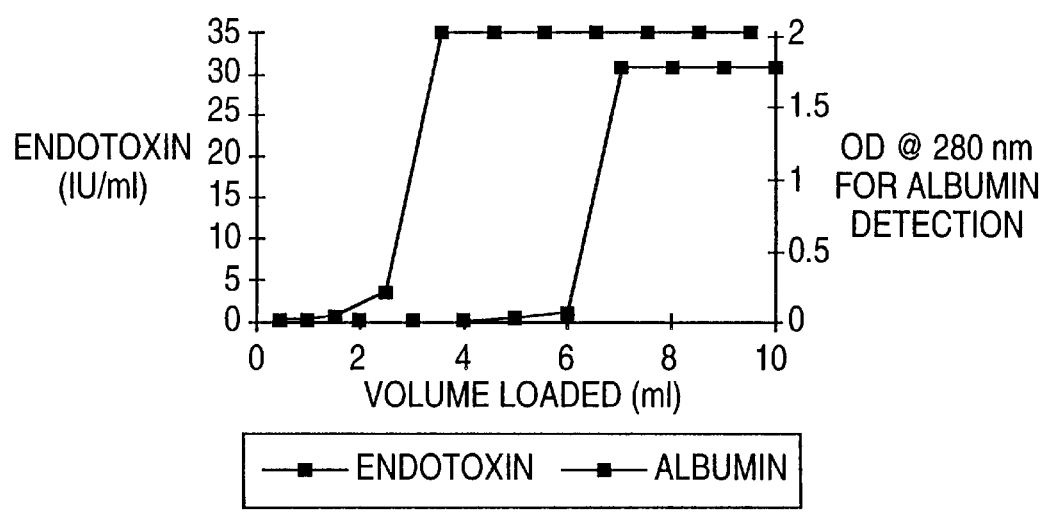
FIG. 2 shows frontal chromatographic analysis of albumin contaminated with endotoxin.

The maximum capacity of the Sephacryl® gel matrices to adsorb endotoxin as determined using frontal analysis. Approximately 10 ml of a 5% w/v albumin solution that had a high endotoxin content was loaded onto the column, and the unbound material was collected in fractions which were subsequently assayed for endotoxin using a Limulus Amoebocyte Lysate (LAL) test kit (Pyrogen Plus, Bio-Whittaker). FIG. 2 illustrates the unbound albumin passing through the column with no endotoxin present up to 6 ml of loading, after which time endotoxin elutes from the column.

Table 3 shows the equivalent endotoxin loads for this run, for which the maximum capacity appears to be 120 EU/ml media (or 4 ml of 30 EU/ml solution).

TABLE 3

Frontal analysis data.

| Volume loaded | Accumulated endotoxin loaded (IU) | Endotoxin level in unbound fractions |
|---|---|---|
| 2 | >60 | <0.06 |
| 4 | 120 | 0.48 |
| 5 | 150 | 0.96 |
| 5.4 | 162 | 31 |
| 5.8 | 180 | 31 |
| 6 | 186 | 31 |
| 10 | 310 | 31 |

This data demonstrates that endotoxin can be successfully removed from an albumin preparation using Sephacryl® S200HR, and that the capacity of this gel matrix to adsorb endotoxins is approximately 120 EU of endotoxin per ml of media.

Example 5

Sephacryl® S200HR (Pharmacia) was packed into a 1 ml column and equilibrated in an acid buffer, 50 mM sodium acetate pH 5.0. A 3 ml aliquot of a 5% w/v albumin solution that had a high endotoxin content was loaded onto the column was then washed with equilibration buffer to recover residual albumin and this was pooled with the unbound albumin. Bound endotoxin was sequently eluted with 1M acetic acid. The recovered albumin pool and the 1M acetic acid eluate were then assayed for endotoxin using a Limulus Amoebocyte Lysate (LAL) test kit (Pyrogent Plus, Bio-Whiftaker). The results are summarised in Table 4 below.

TABLE 4

Endotoxin binding under acidic conditions.

| Load of endotoxin (EU/ml) | Endotoxin in recovered albumin | Endotoxin in 1 M eluate |
|---|---|---|
| >90 | <0.06 | >30.7 |

This data demonstrates the ability of the Sephacryl® S200HR to adsorb endotoxins from an albumin preparation at low pH.

REFERENCES

1. Morrison, D. C. and Ryan, J. L. (1979). Bacterial endotoxins and host immune responses. *Adv. Immunol.* 28, 293.

2. Pearson, F. Chapter 3: Endotoxin, pp 203–218. In *Advances in Parenteral Sciences*/2. "Pyrogens". Editor: J. R. Robinson. Macel Decker Inc. N.Y. (1985).
3. Rietschel, E. T. and Brade, H. Bacterial Endotoxins. *Sci. American* 26–33 August 1992.
4. Weary, M. Chapter 12: Depyrogenation, In *Advances in Parenteral Sciences*/2. "Pyrogens". Editor: J. R. Robinson. Macel Decker Inc. N.Y. (1985).
5. Yap et aL (1993). *Biotechnology of Blood Proteins*, 227, 143–149.

I claim:

1. A process for the removal of endotoxin from a biological product that contains endotoxins, which comprises contacting said biological product with a cross-linked hydrophilic matrix comprising a copolymer of allyl dextran and N,N'-methylene bisacrylamide under conditions effective to bind essentially all endotoxins in said biological product to said matrix, wherein the total amount of endotoxin in said biological product does not exceed the absorptive capacity of said cross-linked hydrophilic matrix, and recovering purified biological product from which endotoxin has been removed as a result of said binding.

2. A process according to claim 1, wherein the cross-linked hydrophilic matrix comprises a product having the partial structure:

3. A process according to claim 2 wherein the cross-linked hydrophilic matrix is selected from Sephacryl® O S200HR, Sephacryl® S300HR, Sephacryl® S400HR, and Sephacryl® S500HR and Senhacryl® S1000SF.

4. A process according to claim 3 wherein the cross-linked hydrophilic matrix is Sephacryl® S200HR.

5. A process according to claim 1, wherein the biological product is a protein for therapeutic use.

6. A process according to claim 5, wherein the biological product is a blood plasma fraction.

7. A process according to claim 6, wherein the biological product is an albumin solution.

8. A process according to claim 1, wherein the biological product is selected from the group consisting of a blood plasma fraction, a recombinant or cell culture expression product, and a fermentation system product.

9. A process for separating a biological product that contains endotoxin by using a regenerable matrix comprising:

(a) contacting the biological product with a cross-linked hydrophilic matrix comprising a copolymer of allyl dextran and N,N'-methylene bisacrylamide under

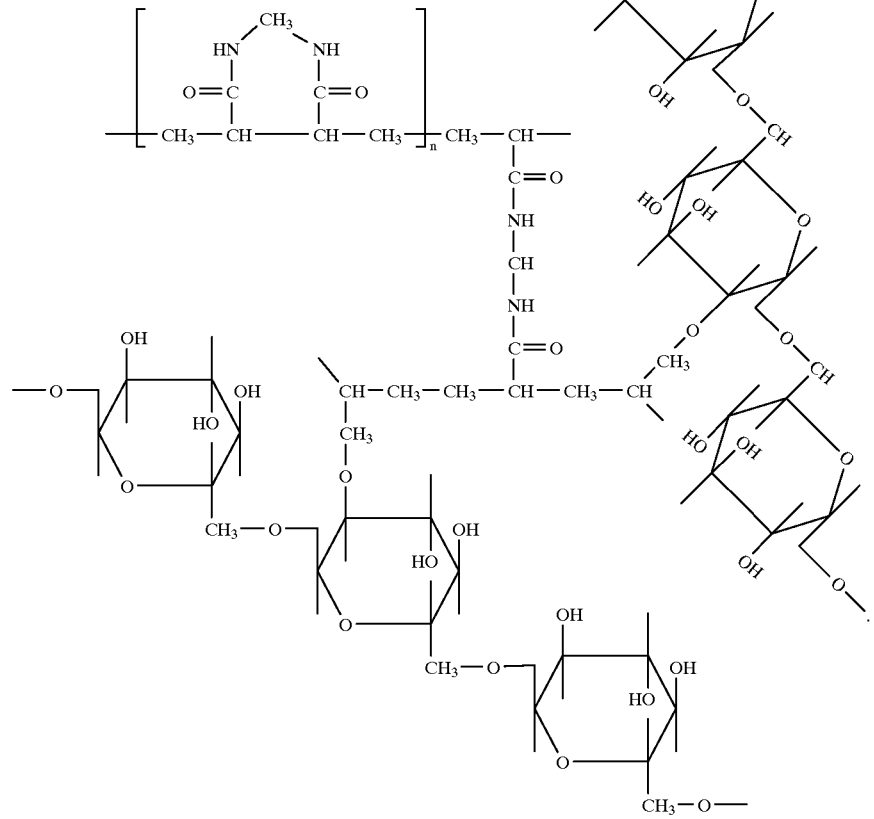

conditions effective to bind essentially all endotoxin in the biological product to said matrix, wherein the total amount of endotoxin in said biological product does not exceed the absorptive capacity of said cross-linked hydrophilic matrix;

(b) eluting purified biological product from the matrix by applying a first solution; and (c) eluting bound endotoxin from the matrix by applying a second solution of lower pH that effectively elutes bound endotoxin from the matrix.

10. The process of claim 9, wherein said second solution comprises 1M acetic acid.

* * * * *